(12) United States Patent
Doyle, II

(10) Patent No.: US 7,128,024 B2
(45) Date of Patent: Oct. 31, 2006

(54) SYSTEM AND METHOD FOR MEASURING ANIMALS

(76) Inventor: John Conan Doyle, II, PO Box 1821, Toowoomba, Queensland (AU) 4350

(*) Notice: Subject to any disclaimer, the term of this patent is extended or adjusted under 35 U.S.C. 154(b) by 0 days.

(21) Appl. No.: 10/619,921

(22) Filed: Jul. 15, 2003

(65) Prior Publication Data

US 2005/0011466 A1    Jan. 20, 2005

(51) Int. Cl.
*A01K 29/00* (2006.01)

(52) U.S. Cl. .................. 119/518; 119/841; 382/110

(58) Field of Classification Search ............. 119/518, 119/842, 51.02, 511, 522, 841; 73/602; 452/157, 452/198; 382/110, 312
See application file for complete search history.

(56) References Cited

U.S. PATENT DOCUMENTS

| | | | |
|---|---|---|---|
| 4,280,448 A | 7/1981 | Ostermann | 119/155 |
| 4,288,856 A | 9/1981 | Liseth | 364/567 |
| 4,617,876 A | 10/1986 | Hayes | 119/155 |
| 4,733,971 A | 3/1988 | Pratt | 366/141 |
| 4,745,472 A | 5/1988 | Hayes | 356/107 |
| 4,785,817 A * | 11/1988 | Stouffer | 600/443 |
| 4,815,042 A | 3/1989 | Pratt | 366/141 |
| 4,889,433 A | 12/1989 | Pratt | 366/141 |
| 4,939,574 A * | 7/1990 | Petersen et al. | 348/89 |
| 5,315,505 A | 5/1994 | Pratt et al. | 364/413.01 |
| 5,339,815 A * | 8/1994 | Liu et al. | 600/437 |
| 5,340,211 A | 8/1994 | Pratt | 366/141 |
| 5,483,441 A | 1/1996 | Scofield | 364/400 |
| 5,576,949 A | 11/1996 | Scofield et al. | 364/401 |
| 5,673,647 A | 10/1997 | Pratt | 119/51.02 |
| 6,591,221 B1 | 7/2003 | Doyle | 702/159 |
| 6,639,352 B1 * | 10/2003 | Eom | 313/493 |
| 6,974,373 B1 * | 12/2005 | Kriesel | 452/157 |
| 2002/0050248 A1 | 5/2002 | Pratt | 119/51.02 |

FOREIGN PATENT DOCUMENTS

| | | |
|---|---|---|
| AU | 744213 | 1/2000 |
| CA | 2216309 | 11/1997 |
| CA | 2335845 | 12/2000 |
| JP | 10-206549 | 8/1998 |
| WO | WO 9967631 | 12/1999 |

OTHER PUBLICATIONS

F.J.C. Swanepoel and H. Heyns, The Influence of Shourlder Height and Body Length on Performance of Simmentaler Bulls, South African Journal of Animal Science undated, vol. 16, pp. 31-35.
D. G. Fox, Using Computer Models in Extension to Develop More Profitable Feeding Systems, Department of Animal Science, Cornell University, obtained from http://www.inform.umd.edu/EdRes/Topic/AgrEnv/n . . . , Feb. 2003, pp. 1-14.

* cited by examiner

*Primary Examiner*—Teri Pham Luu
*Assistant Examiner*—Kimberly S. Smith
(74) *Attorney, Agent, or Firm*—Howrey LLP

(57) ABSTRACT

A system and method for measuring an animal includes a light source and an optical source. The light source, which is preferably an array of monochromatic light emitting diodes, at least partially backlights one or more of the animal's legs. The optical sensor or device, which is preferably a single dimension camera or charged-coupled device, opposes the light source and obtains an image that includes silhouettes of one or more legs of the animal. A processor, such as a computer with software and data storage, determines measurements, such as the approximate skeletal trunk length of the animal, from the silhouetted legs in the image. One or more first ultrasound transducers can be arranged to determine an approximate height of the pelvic region, and one or more second ultrasound transducers can be arranged to determine an approximate width of the pelvic region.

29 Claims, 6 Drawing Sheets

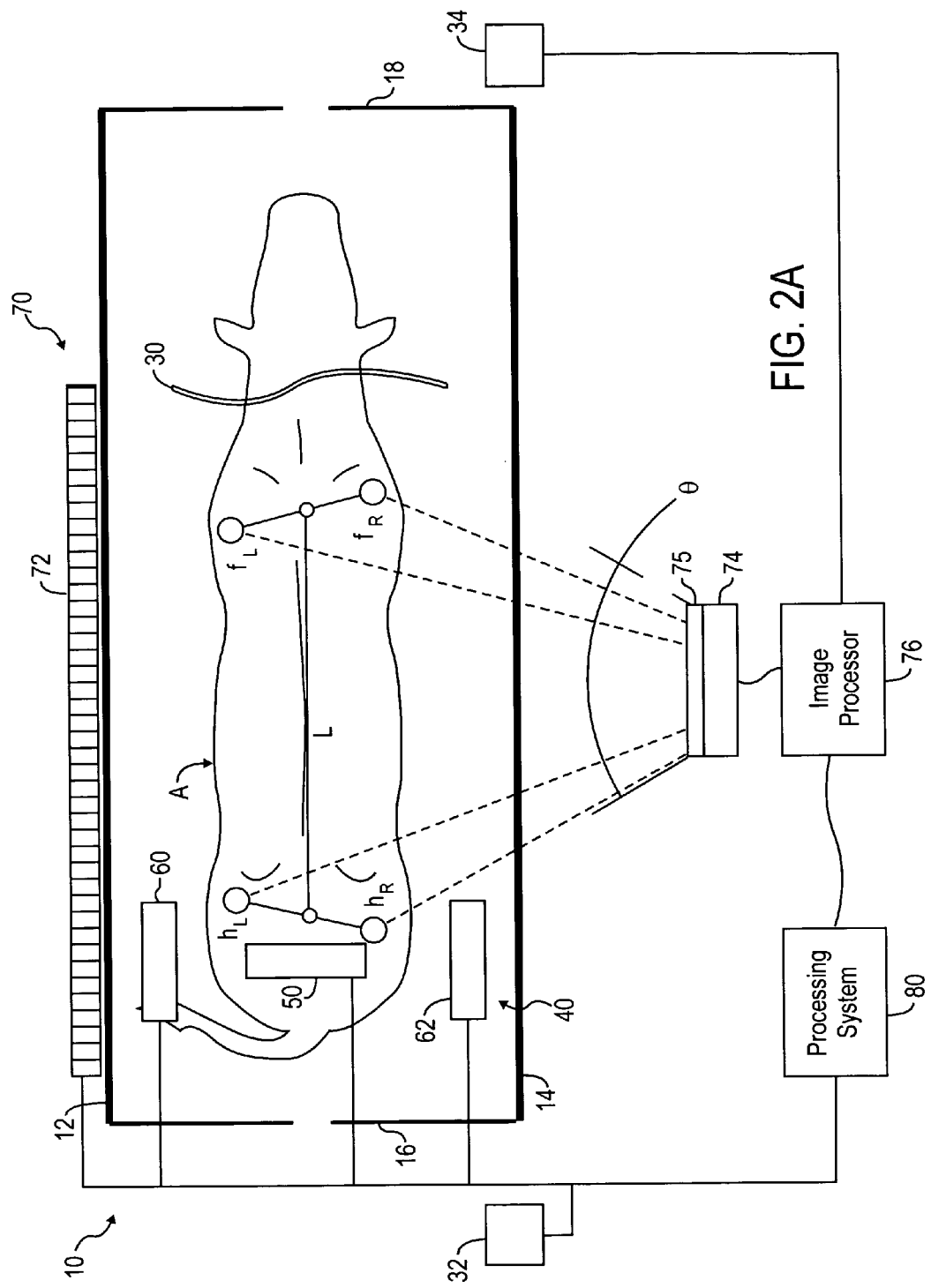

SYSTEM AND METHOD FOR MEASURING ANIMALS

FIELD OF THE INVENTION

The present invention relates generally to a system and method for measuring growth of animals, such as cattle (beef and dairy), sheep, goats, and swine. More particularly, the present invention relates to a system and method for measuring characteristics of an animal's skeletal structure using optical and acoustic devices to determine the growth potential of the animal.

BACKGROUND OF THE INVENTION

Various animals, such as beef cattle, dairy cattle, horses, sheep, goats, and swine, are raised for profit. For beef cattle, for example, it is preferred that the animal attains an optimum endpoint of tissue growth for it to be the most profitable. For a replacement dairy heifer, for example, it is preferred to minimize fat deposition in udder while maximizing bone, organ and muscle tissue. Increasing fat deposition in udder decreases heifers lifetime milking production potential. When considering the optimum endpoint of tissue growth and the optimum rate of growth, it is important to note that the weight at which animals obtain the same chemical composition differs depending on the age, the skeletal size, the sex, or the maturity of the animals. Hence, chemical composition of the animals can be different even when the weight of the animals is the same. Based on their own visual prediction and days on feed of the average meat quality grade or specification for the cattle in a pen, a feedlot manager may sell the entire pen of cattle at one time, for example. As a consequence, a proportion of the beef cattle may have been overfed past optimal fat deposition, whereas some cattle have not been fed to their genetic growth potential or maturity.

It is known in the art that English heifers are very easily overfed because they fatten readily at a light weight. However, Salers, Charolais, and other Continental breeds generally show their best carcass quality characteristics at much heavier weights than English breeds. Thus, some of the cattle may not be marketed at their optimum economic tissue endpoint, taking into consideration live and carcass prices for the cattle, incremental cost of gain to feed the cattle, and discounts for under or oversized carcasses, insufficient, and excess carcass fat on the cattle.

Work done by Dr. John Brethour (The Composition of Growth in Beef Cattle in Honor of Dr. Rodney L. Preston," Texas Tech University, Lubbock, Aug. 2, 1996) and studies completed at Kansas State University indicated that the economic consequences of suboptimal marketing of fed cattle include: 1) costs of % 1/head/day for each day away from optimal marketing date that an animal is under or over fed (greater than 30% of the pen is marketed more than 25 days away from their optimal marketing date); and 2) results in $3.50 per hundred weight (cwt) increased cost of gain throughout the feeding period when marketing cattle greater than 28 days beyond the optimum. However, when cattle are sorted three ways, less than 3% of the cattle in a pen are marketed greater than 20 days from their optimum tissue endpoint. Thus, identifying reliable and effective techniques for optimum economic tissue endpoint will improve end-product quality and consistency and will positively impact profitability of fed cattle.

Currently, optimum endpoints of growth in feedlot animals can be achieved by predicting such things as the incremental cost of gain, the carcass quality, and the yield grade. Equations to predict incremental cost of gain and accounting for differences in net energy for maintenance requirements ($NE_m$) of the animals, the effect of environment on maintenance requirements ($NE_m$), the differences in body size, the implant program and feeding system have been reported in the Journal of Animal Science, Volume 70 by Sniffen et al. (1992; page 3562 to 3577) and Fox et al. (1992; page 3578 to 3596) and in the 1996 NRC model (currently known as the Cornell Net Carbohydrate and Protein System). Equations to predict carcass weight and body composition of different beef cattle breeds finished at three different endpoints have also been reported in the Journal of Animal Science, Volume 69, page 4696 to 4702, by Perry et al. (1991), in the Journal of Animal Science, Volume 72, page 1806 to 1813 by Tylutki et al. (1994), and in the journal of Animal Science, Volume 75, page 300 to 307 Perry and Fox (1997).

In addition, several reports and technologies exist in the art that address the issues of growth and management, particularly in feedlot cattle. For example, U.S. Pat. Nos. 4,733,971; 4,889,433; 4,815,042; 5,340,211; and 5,315,505 to Pratt pertain to the delivery of feed additives and inventory of drugs for feedlot cattle. U.S. Pat. No. 5,673,647, U.S. patent application Ser. No. 08/838,768, and U.S. Patent Application Publication No. 20020050248 disclose automated systems for managing and monitoring cattle. Ultrasound techniques have been developed to measure backfat in cattle by Professor John Brethour as explained in an article entitled "Use of Ultrasound to Estimate Body Composition" presented at a symposium entitled, "The Composition of Growth in Beef cattle in Honor Of Dr. Rodney L. Preston," Texas Tech University, Lubbock, Aug. 2, 1996.

In the art of managing cattle, body weight is commonly used to project feed performance or to estimate economic profitability of the cattle. Techniques for weighing cattle are disclosed in the following U.S. Pat. Nos. 4,288,856; 4,617,876; and 4,280,448. The measurement of animal weight is used because the measuring equipment is relatively simple. However, animal weight is highly variable and thus, represents a poor indicator of animal growth. For example, body weight is sensitive to the volume of water (tissue and gastrointestinal tract content). Measurement of body water and specific gravity are indirect methods of estimating body composition, as reported in the Journal of Biological Chemistry, Volume 158, page 685 to 696 by Pace and Rathbun (1945). Using body water and nitrogen measurements of guinea pigs, the authors concluded that the water content of the lean body mass is 73% and thus should be a reasonable estimate of most species of mammals (Pace and Rathbun, 1945). The drive to measure body water generated the use of various proposed dilution techniques involving deuterium, tritium, antipyrine, and urea. The decrease in body weight due to water loss is termed "shrink" and is well recognized in the beef industry.

Not only is the amount of weight loss an animal experiences dependent upon recent water intake, but also it is dependent upon other factors, such as feed intake and stresses related to transport or sickness. Furthermore, cattle are fed differently around the world so that the percentage of empty body weight due to fat deposits (empty body weight fat percentage is sometimes referred to as empty body weight fat) and the maturity of the animals can vary dramatically from place to place. As an example, cattle of similar age, sex, breed, and weight are fed either low or high-energy ration. These cattle will both grow similar skeletal, organ, and muscle deposits. However, the cattle fed low energy ration will possess lower empty body weight fat percentage, whereas cattle fed the high energy ration will possess higher levels of empty body weight fat, have heavier weights because of additional fat, and have an eventual higher carcass dressing percentage.

Skeletal measurements of the cattle can avoid some of the transient factors associated with merely measuring the weight of the animals discussed above because changes in an animal's skeleton are independent of feed and/or water intake and transient environmental stress. As an animal grows and metabolizes nutrients, tissues are deposited through the following sequential series from first to last: nervous system, bone tissue, organ tissue, muscle tissue, and fat. In addition, tissues are deposited from the cranial to caudal region of the animal from first to last: head, neck, thorax, rump, loin, and rib area. Bone tissues that are deposited as skeletal structure regulate muscle deposition, red blood cell production, and various immunological factors and can, therefore, be a suitable determining factor of an animal's growth potential. Furthermore, skeletal measurements are not influenced by water loss or adequacy and are, therefore, a more adequate method to define the body size of the animal. In addition, the author's own research has shown that skeletal pelvic height has a high correlation to finished carcass weight for the animal compared to entry and finished weights for cattle fed over a 70-day period.

Physical measurements including pelvic measurement can be used to estimate animal characteristic, such as potential skeletal and muscle development. Typical parameters used in such estimates are hip height and width, shoulder width, and body length. Measurements of these parameters can be used to calculate shoulder muscle to bone ratio, rump muscle to bone ratio, and musculoskeletal development per unit height and length. It is believed that skeletal size or hip height of cattle can be correlated with the ultimate carcass weight of the cattle fed for a 70-day period. It is also believed that the shoulder height and the body length of cattle can be used to determine the potential average daily gain and feed conversion to final body weight of the cattle.

Unfortunately, making manual measurements of the cattle's shoulder height and body length are time consuming and less reliable. Moreover, determining points on the cattle for making such manual measurements are not well defined on the 3-dimensional animals. It is known in the art to use a conventional 2-dimensional video camera to obtain an image of the animal. The image taken with the 2-dimensional video camera, however, is not particularly useful for determining the skeletal trunk size of the animal. The image includes body mass from muscle and fat and can be confounded by lighting conditions and the hide color of the animal, for example, making it difficult to differentiate the body tissue composition (bone, muscle & fat) of the animal. For example, the anatomical juncture of the neck with the shoulder (i.e., major tubercle of humers or "point of shoulder") is not well defined in such an image made with a 2-dimensional video camera because muscles in this anatomical region of the neck make it difficult to distinguish the skeletal elements of the major tubercle of humerus.

Another method of measuring animals uses ultrasound technology. Suitable teachings of measuring animals with the ultrasound technology are disclosed in WO99/67631, AU744213, AU449219, and CA2335845, which are incorporated herein by reference in its entirety. The reader is also referred to the following references that describe techniques for measuring animals: U.S. Pat. Nos. 4,745,472; 5,483,441 and 5,576,949, CA 2216309; and JP 10206549.

Although the techniques discussed above are useful, feedlot managers or operators are constantly seeking to improve measurement and management techniques for animals. Accordingly, a need exists in the art for accurate techniques to measure the skeletal structure of animals that can enhance a feedlot manager's ability to manage the animals to an optimum economic endpoint, thus avoiding discounts for too much fat and outsized carcasses and avoiding the economic consequence of suboptimal marketing of cattle (e.g., increased cost of gain).

The present invention is directed to overcoming, or at least reducing the effects of, one or more of the problems set forth above.

SUMMARY OF THE PRESENT DISCLOSURE

A system and method for measuring an animal includes a light source and an optical sensor or device. The light source and optical sensor are arranged to oppose one another and can be mounted in sidewalls of a measurement unit. The light source backlights a portion of the animal's legs. In one embodiment, the light source is a plurality of light emitting diodes arranged in an array. The optical sensor obtains an image that includes silhouettes of the portion of the animal's legs. In one embodiment, the optical sensor is a charged-coupled-device or a single dimension video camera. A processor, such as a computer with software and data storage, can analyze the silhouetted legs on the image to determine the skeletal trunk length of the animal. One or more first ultrasound transducers can be arranged to determine an approximate height of the animal's pelvic region. In addition, one or more second ultrasound transducers can be arranged to determine an approximate width of the animal's pelvic region. The disclosed system and method can be used to identify differences in skeletal changes of animals through repeated measurements over the life of the animals. Animals can be individually identified early in life and can then be monitored for changes in skeletal growth over various time periods throughout their lives.

The foregoing summary is not intended to summarize each potential embodiment or every aspect of the invention disclosed herein.

BRIEF DESCRIPTION OF THE DRAWINGS

The foregoing summary, preferred embodiments, and other aspects of the subject matter of the present disclosure will be best understood with reference to a detailed description, which follows, when read in conjunction with the accompanying drawings, in which:

FIG. 2A illustrates a detailed plan view of the disclosed system of FIG. 1.

Figure 1:
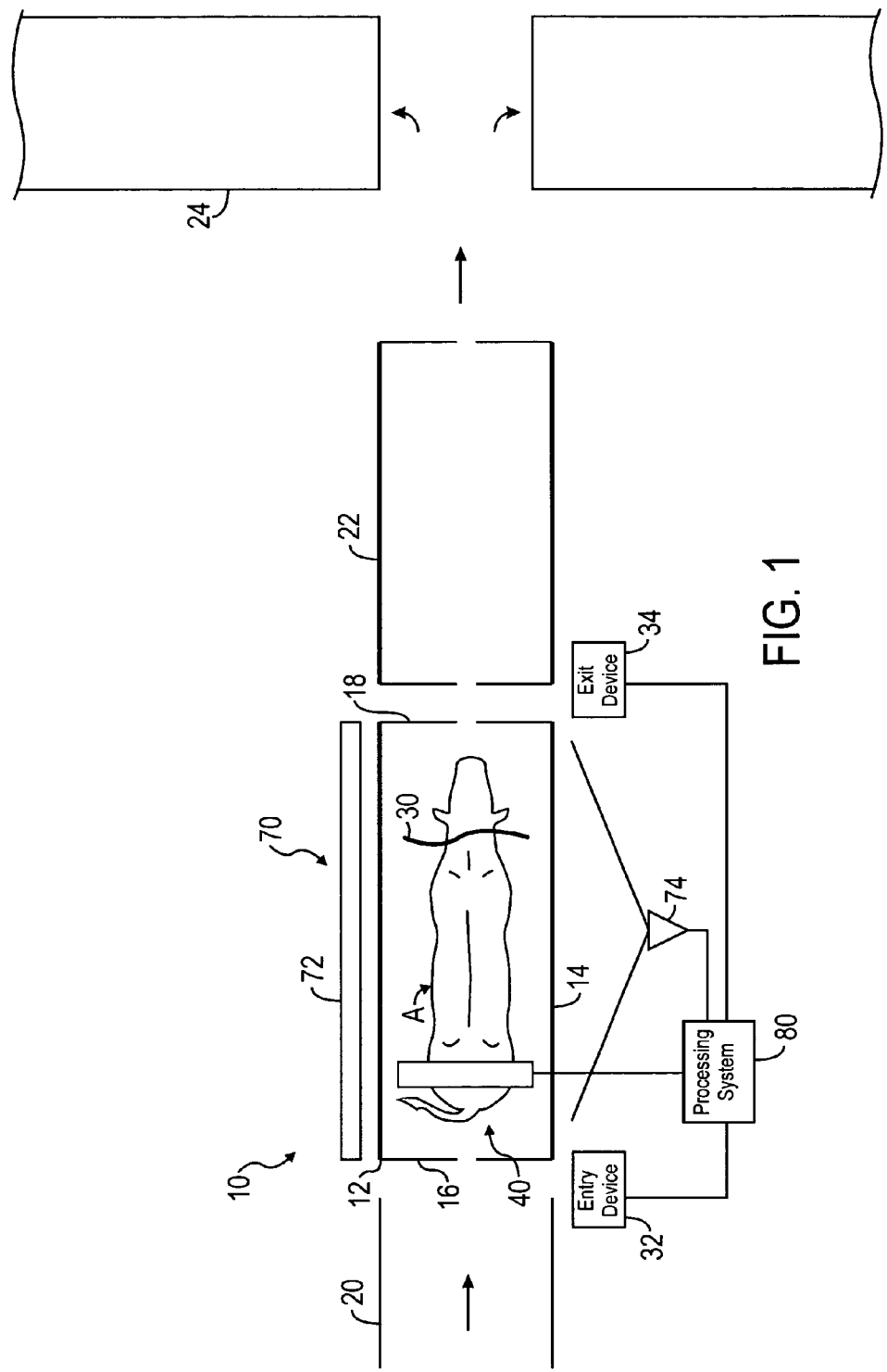
FIG. 1 illustrates a plan view of an animal disclosed system according to certain teachings of the present disclosure.

While the disclosed system and method are susceptible to various modifications and alterative forms, specific embodiments and inventive concepts of the disclosed system and method have been shown by way of example in the drawings and are herein described in detail. The figures and written description are not intended to limit the scope of the disclosed inventive concepts in any manner. Rather, the figures and written description are provided to illustrate the disclosed inventive concepts to any person skilled in the art by reference to particular embodiments, as required by 35 U.S.C. § 112.

DETAILED DESCRIPTION

Referring to FIG. 1, an embodiment of an animal disclosed system 10 for making a number of measurements of animals, such as cattle, is schematically illustrated in a plan view. The disclosed system 10 can be used in conjunction with common devices for directing and sorting animals, such as an alleyway 20, squeeze chute 22, and sorting pens 24. The disclosed system 10 is constructed to allow a single animal A to enter, stand, and exit the disclosed system 10 at one time. In one embodiment, for example, the disclosed system 10 has a rectangular framework with sidewalls 12 and 14 of approximately 2.5-m long and 2.0-m high. An entry point or posterior door 16 and an exit point or anterior door 18 are attached to the sidewalls 12 and 14 to control the entry and exit of the animal A. The anterior dorsal aspect of the disclosed system 10 can be fitted with an adjustable flap 30 to block anterior advancement of a smaller animal and to keep the caudal region of the animal near the posterior door 16. Alternatively, the unit can have other devices to position the animal in the unit that use light, sound, hydraulics, or compressed air, for example. Because the disclosed system 10 is used in the handling, sorting, and confinement of animals, it is preferably constructed using the common techniques known in the art for such structures.

To allow the animal to enter, the posterior door 16 is opened manually or automatically. As the animal enters or stands in the disclosed system 10, the identity of the animal can be assigned by management, determined visually or electronically using methods known in the art. The information can include the animal's lot or identification number, age, sex, breed, market classification, domestic information relating to growth hormones, frame score, and any other pertinent information relating to the animal. For example, an ear tag on the animal may have an identification number, which can be input manually by an operator. In addition, the disclosed system 10 of the present disclosure can be used with existing systems for managing feedlot animals, such as computer systems known in the art that can automatically identify individual animals for handling and sorting. Information of the animal can be detected by an entry device 32 and automatically input into the processing system 80. For example, the entry device 32 can perform infrared analysis of a bar coded tag on the animal. The entry device 32 can also be programmed to record signals from internal or external transponders on the animal. Such transponders for identifying animals are known in the art. Preferably, information, such as age, sex, breed, and the like are stored in the processing system 80 so that there is no need for these values to be re-entered when the animal is re-measured.

After the animal enters, the posterior door 16 is shut, and the adjustable flap 30 is moved to keep the caudal region of the animal near the posterior door 16. The flap 30 can be controlled by an operator or can be operated automatically. While the animal is in the disclosed system 10, a number of devices make external measurements of the animal for later determination of the animal's skeletal structure, which are described below. The disclosed system 10 can have a scale (not shown) in the floor or can be adapted for use with an existing weight scale. Alternatively, the weight of the animal can be determined at a different site and the information recorded or input into the processing system 80, as desired.

The disclosed system 10 also includes a sensing system 40 and an imaging system 70. The sensing system 40 is used for measuring the pelvic height $H_P$ and pelvic width $W_P$ of the animal and preferably includes a plurality of ultrasound transducers 50, 60, and 62 detailed in FIG. 2A. In addition to measuring the pelvic height Hp of the animal, the sensing system 40 could similarly measure the height and/or width of the animal at the shoulder as well. The imaging system 70 is used for measuring the skeletal trunk length L of the animal and preferably includes a light source 72, an optical device or sensor 74, and an image processor 76. As described in more detail below, the sensing system 40 and the imaging system 70 of disclosed system 10 externally and non-invasively obtain skeletal measurements of the animal without restraining the animal or making physical contact with the animal. Depending on a particular implementation and facility, the various measuring devices of the sensing system 40 and the imaging system 70 can be activated manually by an operator. Alternatively, the various measuring devices can be automatically triggered by the posterior door 16 opening, by the application of weight on the scale, or by activation of an infrared sensor or motion detector, for example.

When measurements have been obtained with the scale, the sensing system 40, and the imaging system 70, the processing system 80 has the different data from the individual devices (e.g., electronic identification from the entry device 32, distances from the ultrasound transducers 50 and 60, 62, the image from the imaging system 70, weight from the scale, etc.). The animal is then allowed to exit the disclosed system 10. The adjustable flap 30 is moved, and the anterior door 18 is opened either manually or automatically. An exit device 34 can mark or otherwise tag each animal with an identifier as it exits the disclosed system 10. For example, the exit device 34 can mark the exiting animals with different color paints for visual identification. In another example, the exit device 34 can add electronic information to electronic ear tags on the animals, can add visual information to non-electronic ear tags on the animals, or can provide other identifiers by which individual animals can be identified later. Such identification devices for tagging or marking animals are known in the art and can be used for later managing, feeding, and sorting the individual animals. Topical insecticides and anti-parasite drugs can also be administered from devices as the animal exits the disclosed system 10.

Once the animal exits the disclosed system 10, the animal can then enter the squeeze chute 22 (e.g. to apply identification on the animal when required) and can be positioned to move forward to animal drafting and sorting pens 24. When animals are being processed for the first time, they may not have any identification when entering the unit for measurements. In such a case, first measurements can be initially obtained with the unit and can be stored in the processing system 80. Once identification, such as an electronic ID, bar coded ear tag, or numbered ear tag, is administered or attached to the animal, they can be generally sorted into pens. The second time these animals enter the unit, which could be about 70 days later, for example, they will have their identification and will be measured a second time for further evaluation. For example, the difference in the first and second measurements (i.e., weight, skeletal length, pelvic height, and pelvic width) can be used to determine and assign a specific implant treatment and/or feeding program. Consequently, selection of particular sorting pens for the exiting animals based on the measurements obtained with the disclosed system 10 can be used to place individual animals with particular, measured characteristic and known information in a sorting pen having animals with similar characteristics. Sorting the animals in this way can enable a feedlot manager to apply various regimens of feed, growth promotants, and the like to particular animals or groups of animals, depending on their age, breed, sex, skeletal structure, etc. The animals sorted into various groups can be fed the same rations so that they efficiently and effectively obtain substantially the same tissue composition.

Figure 2B:
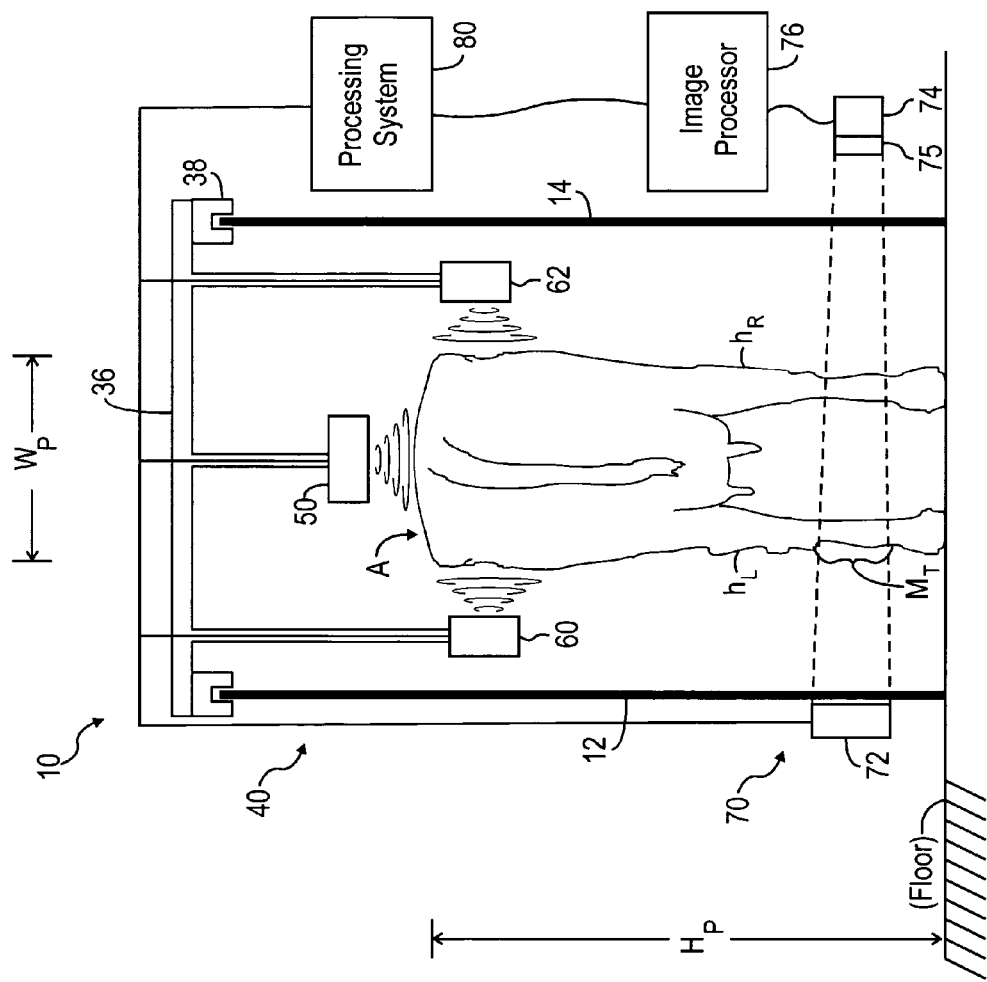
FIG. 2B illustrates an end view of the disclosed system, showing the imaging system and one arrangement of the acoustic devices.

Referring to FIG. 2A-B, more detailed plan and end views of the disclosed system 10 of FIG. 1 are illustrated, showing an animal A within the disclosed system 10. As alluded to above, the sensing system 40 and the imaging system 70 make external measurements of the animal for later determination of the animal's skeletal structure size or coefficients. A processing system 80 is coupled to the sensing system 40 and the imaging system 70 and processes data from these systems 40 and 70. The processing system 80 can also be coupled to the other components of the disclosed system 10, including the entry device 32 and exit device 34, for example. In one embodiment, the processing system 80 can include a computer having appropriate software and data storage. In an alternative embodiment, the processing system 80 can be controlled by a manager through an office communication or a computer link. In other words, decision on how to draft, manage, or administer to the animals can be made by remote office decisions that set particular parameters.

The sensing system 40 preferably includes one or more acoustic devices 50 and 60, 62 for measuring distances to the pelvic region of the animal A. As described in more detail below and as best shown in FIG. 2B, the distances measured with the acoustic devices 50 and 60, 62 are then used to determine the approximate pelvic height $H_P$ and pelvic width $W_P$ of the animal. The imaging system 70 preferably includes a light source 72, an optical sensor 74, and an image processor 76 for determining the position of the animal's legs $h_L$, $h_R$, $f_L$, and $f_R$. As described in more detail below and as best shown in FIG. 2A, the positions of the animal's legs $h_L$, $h_R$, $f_L$, and $f_R$ are then used to determine the approximate skeletal trunk length L of the animal.

As best shown in the end view of FIG. 2B, the light source 72 is installed near the bottom of the first sidewall 12. The light source 72 can be a linear array of lights, such as an array of monochromatic light emitting diodes (LEDs) with diffusers. The optical sensor 74 is opposed to the light source 72 and is installed in the second sidewall 14. The optical sensor 74 is preferably a single dimension video camera or linear charged-coupled-device. Preferably, the light source 72 and optical sensor 74 are arranged to view the legs of the animal A in the location of the metacarpus (not shown in FIG. 2B) on the forelegs and the metatarsus $M_T$ of the hind legs $h_{L-R}$ of the animal. A lens 75 can be used to limit the vertical field of view of the optical sensor 74. In the opposing arrangement of the present embodiment, the light source 72 backlights the legs of the animal so that the optical sensor 74 can capture a well-defined, contrasted image of the position of the legs. Although not preferred, the light source 72 may be arranged to illuminate the legs from the same side of the disclosed system as the optical sensor 74, and the image processor 76 coupled to the optical sensor 74 may include filters to improve the definition and contrast of the captured image.

As best shown in the plan view of FIG. 2A, the light source 72 and optical sensor 74 are preferably arranged to view the legs of the animal in a field of vision θ ranging from about 45° to 60°. To allow the optical sensor 74 to view a substantial portion of the bottom length of the disclosed system 10, the optical sensor 74 can be positioned laterally away from the sidewall 14 of the disclosed system 10. Although the optical sensor 74 is preferably a single dimension video camera or linear charged-coupled-device; a photodiode array, a CMOS optical sensor, a still photographic camera, a digital camera, a conventional 2-dimension camera, or other image device can be used as long as the same information of the positions of the animal's legs detailed below can be obtained as with the preferred single dimension video camera or linear charged-coupled-device. Use of a conventional 2-dimension camera, for example, may require processing and truncating of the image to produce an image comparable to a single dimension video camera or linear charged-coupled-device.

Figure 3A:
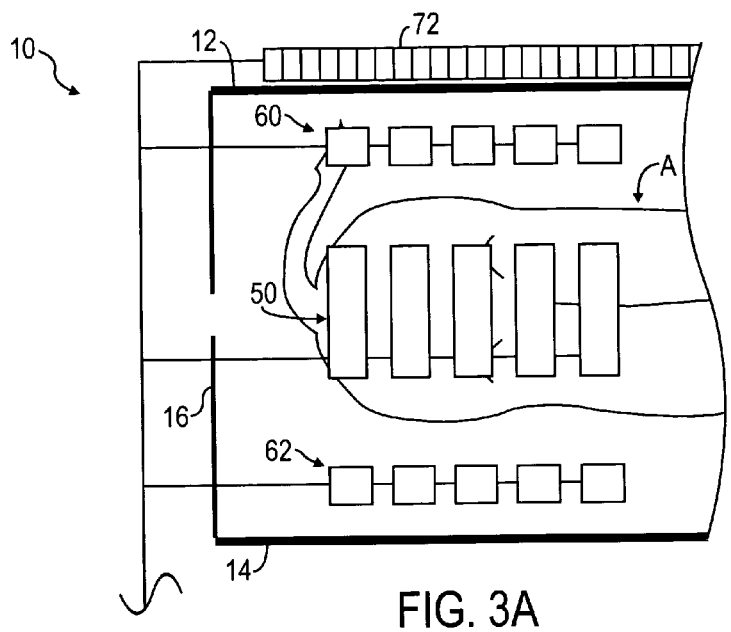
FIG. 3A illustrates a plan view of the disclosed system, showing another arrangement of the acoustic devices.
Figure 3B:
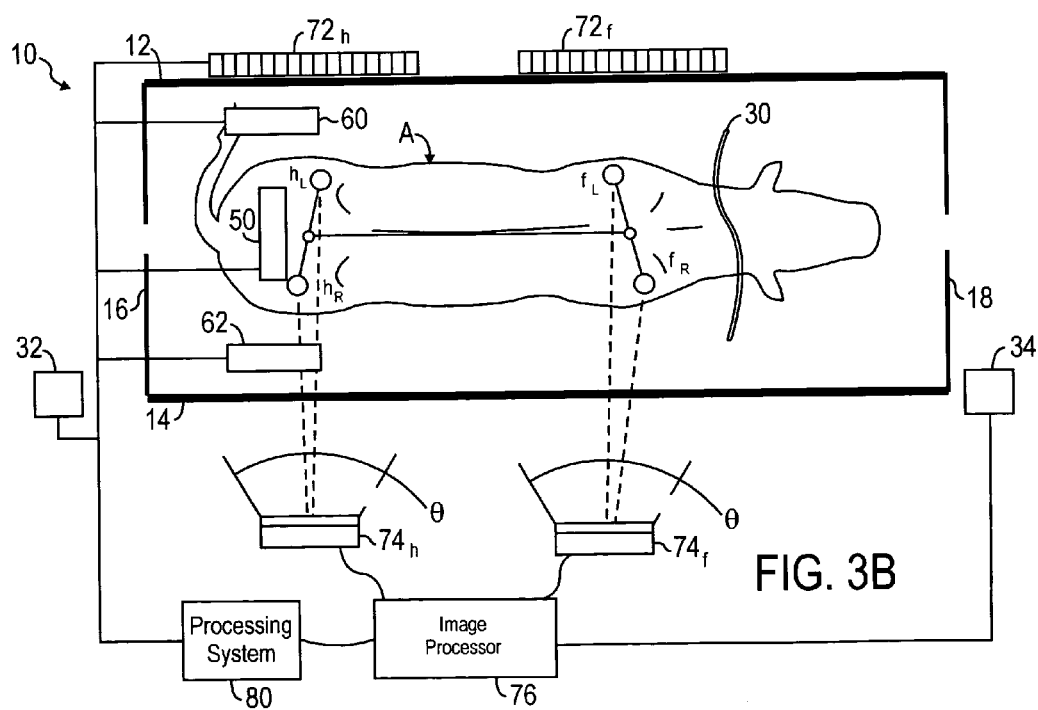
FIG. 3B illustrates a plan view of the disclosed system, showing another arrangement of the optical sensors.

In an alternative arrangement to the embodiment of FIG. 2A-B, the disclosed system 10 as embodied in FIG. 3B can include first and second light sources $72_f$ and $72_h$ respectively positioned in the first sidewall 12 at the general locations of the forelegs $f_{R-L}$ and hind legs $h_{R-L}$ of the animal A. In addition, the disclosed system 10 as embodied in FIG. 3B can include first and second optical sensors $74_f$ and $74_h$ opposing these dual light sources $72_f$ and $72_h$. The teachings disclosed herein for the embodiment of FIGS. 2A–B can be readily applied to this alternative arrangement of dual light sources $72_f$ and $72_h$ and optical sensors $74_f$ and $74_h$ illustrated in FIG. 3B.

Returning to the embodiment of FIGS. 2A–B, the imaging system 70 monitors the leg movement and position of the legs $h_L$, $h_R$, $f_L$, and $f_R$, as the animal enters and stands in the disclosed system 10. The output signals from the optical sensor 74 are sent to the image processor 76, which can include optical train and background filters, among other components known in the art of image processing. The positions of animal's legs are accepted or rejected based on clarity, resolution, and other factors. A light signal, audio signal, visual display, or other like indicator, for example, can provide an operator of the disclosed system 10 with an indication that the imaging system 70 has successfully captured a measurable image of the animal's legs $h_L$, $h_R$, $f_L$, and $f_R$. The data from the imaging system 76 is then sent to the processing system 80 for analysis. As noted above, the processing system 80 can be a computer having software and, therefore, can include components and software for the image processor 76 as well.

While the animal is in the disclosed system 10, the acoustic devices 50 and 60, 62 measure distances to the pelvic region of the animal. As alluded to above, the sensing system 40 could include acoustic devices to measure the height and/or width of the animal at the shoulder, if desired. For example, one or more acoustic devices could be arranged or moved near the shoulder region of the animal for measuring distances to the shoulder region and obtaining shoulder measurements in a similar fashion to that disclosed herein for obtaining pelvic measurements. Activation of the acoustic devices 50 and 60, 62 can be done manually by an operator. For example, an operator can observe that the animal is in place and that the imaging system 70 has captured a measurable image. Then, the operator can manually activate the acoustic devices 50 and 60, 62. Alternatively, activation of the acoustic devices 50 and 60, 62 can be done automatically. For example, the processing system 80 can automatically activate the acoustic devices 50 and 60, 62 when a measurable image is captured with the imaging system 70. Alternatively, the disclosed system 10 can include an infrared detector or other device that can detect when an animal is in a certain position within the disclosed system 10.

The acoustic device 50 is preferably used to measure the vertical distance to the top of the pelvis, because this is typically the tallest part of the animal's body. The other acoustic devices 60, 62 are preferably used to measure lateral distances to the pelvic region. The distances measured with the acoustic devices 50 and 60, 62 are then used to determine the approximate pelvic height $H_P$ and width $W_P$ of the animal. The acoustic devices 50 and 60, 62 preferably include ultrasound transducers known in the art. Suitable teachings for using ultrasound transducers and measuring distances to animals are disclosed in WO 99/67631 (now issued as U.S. Pat. No. 6,591,221), which is incorporated herein by reference in its entirety.

To measure a vertical extent of the pelvic region on the animal and ultimately obtain the approximate pelvic height $H_P$, the ultrasound transducer 50 is positioned dorsally above the animal near the posterior door 16. In the embodiment of the disclosed system 10 shown in FIG. 2A, only on ultrasound transducer 50 has a fixed location in the disclosed system 10 and can be able to detect reflected ultrasound signals from the pelvic region of the animal under most circumstances. As detailed below and as best shown in FIG. 2B, the pelvic height $H_P$ of the animal is calculated by the difference between the distance between the ultrasound transducer 50 and the animal and the known distance between the ultrasound transducer 50 and the floor of the disclosed system 10.

As is known, a typical ultrasound transducer generates, amplifies, and transmits a signal, which is reflected from the animal and returns to the transducer. The signal is received, amplified, and processed to provide information as to the distance of a location on the animal's surface to the transducer. For the disclosed system 10, the output for the ultrasound transducer 50 preferably directs a 1-ms tone burst, producing a sound pressure level at about 50 kHz of approximately 118-dB SPL at 1 meter. Typically, the distance between the animal and the ultrasound transducer 50 may then be measured within 1 to 2 seconds or less.

The ultrasound transducer 50 is located above the animal so as to direct an ultrasonic signal towards the dorsal section of the animal's pelvic region. When the pelvic height $H_P$ is being measured, the animal is preferably measured in a freestanding position. Because the animal is allowed to stand freely within the disclosed system 10, the relative vertical location of the ultrasound transducer 50 relative to the pelvis may vary along the length of the animal. However, the ultrasound transducer 50 preferably generates ultrasonic signals that are conical in shape and are incident in a circular manner on the animal. The ultrasonic signals generated by the ultrasound transducer 50 can have a diameter of between about 20-cm and about 60-cm. Preferably, the ultrasonic signals generated by the ultrasound transducer 50 has a diameter between 35-cm and 50-cm and more preferably about 40-cm.

It is believed that with these conditions at least some of the generated signal will reflect from the desired location of the pelvis under most circumstances. In addition, it is preferred that the processing system 80 is able to calculate the distance between the ultrasound transducer 50 and the highest point on the animal that reflects a signal. Thus, it may not be necessary for the animal to be precisely positioned such that the pelvis is directly aligned with the ultrasound transducer 50. Animals having lengths within a certain range, therefore, can be measured with the single ultrasound transducer 50 being located in the same position. The range of lengths of the animals that can be measured in this way may depend on the diameter of the ultrasonic signal and the angle at which the signal is directed towards the animal. To measure animals outside a particular range, ultrasound transducer 50 may be mounted to a track or guide to enable it to be moved along the length of the animal to the desired pelvic region. As best shown in FIG. 2B, for example, the ultrasound transducer 50 can be mounted on a rack 36 with rollers 38 or the like. Thus, the ultrasound transducer 50 can be able automatically or manually moved relative to the pelvic region of the animal to make the vertical measurement. A motor and a drive or an air ram (not shown) can also be used to automatically move the rail 36 and the ultrasound transducer 50. The ability to adjust the position of the ultrasound transducer 50 can be desirable if the ultrasound transducer 50 is intended to measure animals of various size differences, for example. In an alternative embodiment shown in FIG. 3A, a plurality of ultrasound transducer 50 can be fixedly mounted in the disclosed system 10 for making vertical measurements at various points along the length of the disclosed system 10.

To measure a lateral extent of the pelvic region on the animal and ultimately obtain the approximate pelvic width $W_P$, a pair of acoustic devices 60, 62, preferably ultrasound transducers, are positioned laterally on both sides of the animal's pelvic region near the posterior door 16. In the embodiment shown in FIG. 2A, the pair of opposing ultrasound transducers 60, 62 can be fixedly mounted in the disclosed system 10 and capable of measuring distances to the animals pelvic region in a manner similar to that described above. As shown in FIG. 2B, the pair of opposing ultrasound transducers 60, 62 can alternatively be mounted on the rail 36 having wheels 38 so that the ultrasound transducers 60, 62 can be automatically or manually moved relative to pelvic region of the animal to make lateral measurements. In yet another alternative shown in FIG. 3A, a plurality of opposing ultrasound transducers 60, 62 can be fixedly mounted in the disclosed system 10 for making lateral measurement. In these arrangements, the lateral ultrasound transducers 60, 62 are preferably positioned in vertical alignment with the vertical acoustic device 50 so that they measure substantially the same area of the pelvic region of the animal.

Because the disclosed system 10 includes two or more ultrasound transducers 50 and 60, 62, it is preferred that the signals from the respective transducers do not interfere with each other. This may be achieved by programming the transducers 50 and 60, 62, to generate ultrasonic signals in an alternating manner. Alternatively, the measurements can be made separately and sequentially. This can be conducted by either measuring the animal sequentially as it stands in a single location or by measuring one dimension with one transducer (e.g., 50) in a first position and then moving the animal to a second position for a second measurement to be taken with other transducers (e.g., 60 and 62). Of course, conducting the measurements in this manner would require the disclosed system 10 to be longer than shown in the Figures.

Figure 4A:
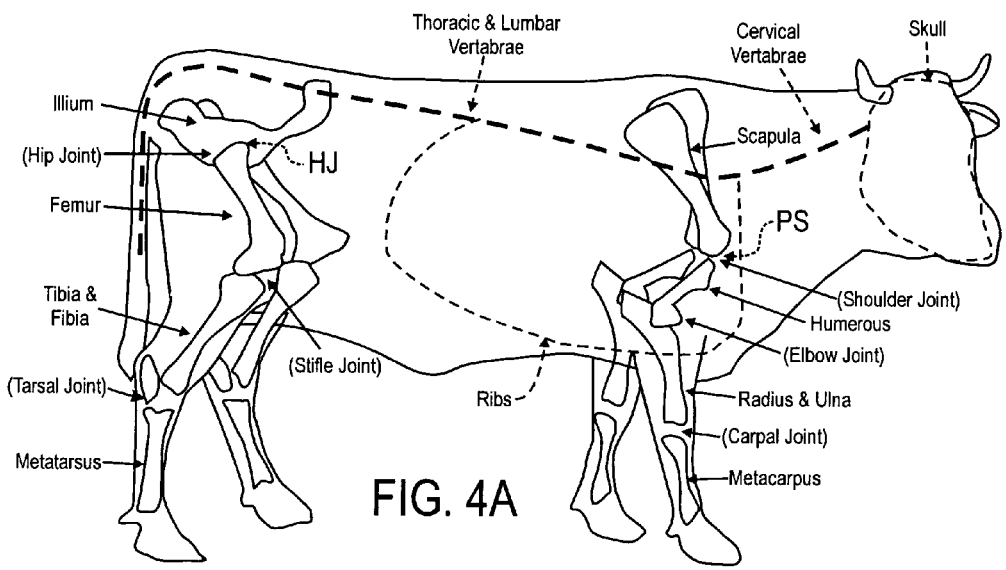
FIG. 4A illustrates skeletal structure of cattle.
Figure 4B:
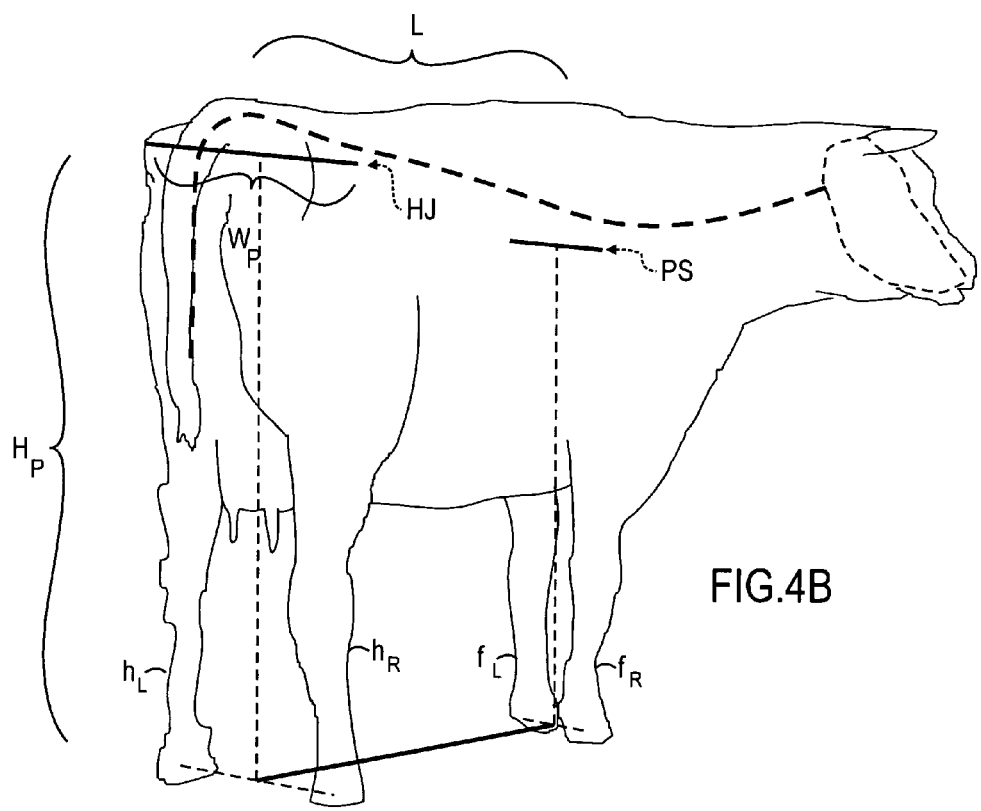
FIG. 4B illustrates the correlation between the measurements from the disclosed system and the dimensions of cattle.

Referring to FIGS. 4A–B, aspects of the skeletal structure of cattle and the measurements made with the disclosed system 10 are illustrated. In FIG. 4A, some of the skeletal structure of a cow is shown by way of example and is not intended to limit the sex or age of the cattle. In FIG. 4B, the correlation between the measurements obtained with the disclosed system 10 of FIGS. 1–3B and the dimensions of the cow's skeletal structure are schematically shown. As best shown in FIG. 4A, the cranial skeletal trunk aspect (front) of the animal is defined by the major tubercle of the humerus or "point of shoulder" PS. The caudal aspect (rear) of the animal, such as the pelvic ischiatic tuber or tail posterior, is a less well-defined anatomical point on cattle. Muscle, fat, and the extension of the tail in the caudal aspect can distort measurement in the rump or pelvic area. The disclosed system provides an accurate assessment of animal skeletal trunk length L or center of gravity when the animal is in a natural stance or is in motion (e.g., walking or stepping).

As best shown in FIG. 4B, the cow's natural center of gravity for the foreleg pair $f_{L-R}$ lies approximately at the mid-point distance between forelegs $f_{L-R}$. This midpoint is substantially perpendicular to the point of shoulders PS of the animal. The cow's natural center of gravity for the hind leg pair $h_{L-R}$ lies approximately at the mid-point distance between hind legs $h_{L-R}$. This hind midpoint is also substantially perpendicular to major trochanters of the femurs (hip joints) HJ on the pelvic region of the animal. Therefore, an approximate skeletal trunk length L for the cow can be obtained by determining the distances between midpoints of the foreleg pair $f_{L-R}$ and the hind leg pair $h_{L-R}$. Measuring the position and distances between the legs $h_{L-R}$ and $f_{L-R}$ of the animal is readily repeatable. Furthermore, the legs $h_{L-R}$ and $f_{L-R}$ are not disguised by muscle, fat, and other external features of the animal, making optical measurement reliable.

Figure 5:
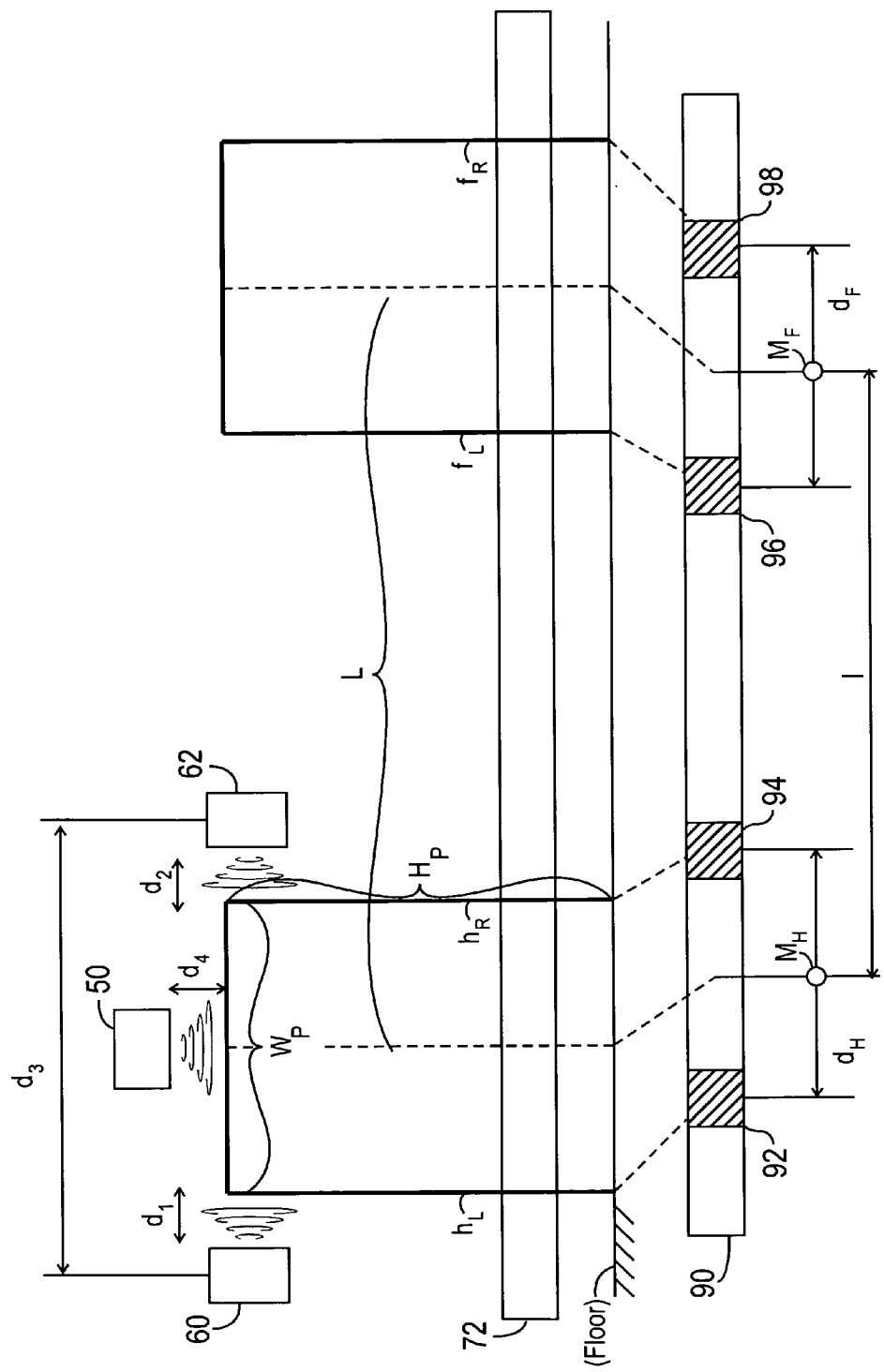
FIG. 5 diagrammatically illustrates measurements taken with the disclosed system according to certain teachings of the present disclosure.

Referring to FIG. 5, the measurement process that occurs in the disclosed system 10 briefly described above is diagrammatically shown. With the animal in the disclosed system 10, the imaging system 70 having the opposing light source 72 and the optical sensor (not shown) is used to produce an image 90 of the lower portion of the animal's legs $h_L$, $h_R$, $f_L$, and $f_R$. Because the linear monochromatic light source 72 is located opposite the optical sensor (not shown), the light source 72 backlights the position of the animal's legs $h_L$, $h_R$, $f_L$, and $f_R$. The resulting image 90 has silhouettes 92, 94, 96, and 98 of the individual legs $h_L$, $h_R$, $f_L$, and $f_R$ of the animal A. Preferably, the light source 72 and optical sensor are positioned at a level to produce an image of the region of the cattle's legs $h_L$, $h_R$, $f_L$, and $f_R$ having the metacarpus and metatarsus bones, best shown in FIG. 4A.

The average separations or midpoints between the legs in each pair of silhouettes 92, 94 and 96, 98 are used to identify cranial and caudal extent (skeletal trunk length L) of the animal. On animals and more particularly on cattle, the midpoint $M_F$ between the fore leg pair $f_{L-R}$ is substantially perpendicular to the cranial skeleton region (i.e., major tubercle of humerus or point of shoulder PS of FIGS. 4A–B). In addition, the midpoint $M_h$ between the hind leg pair $h_{L-R}$ is substantially perpendicular to the caudal skeleton region (i.e., the major trochanter of femur or hip joints HJ in FIGS. 4A–B). The distance between these midpoints $M_H$ and $M_F$ is proportionate to the approximate skeletal trunk length L of the animal (i.e., the distance L best shown in FIG. 4B from the major trochanter of femur PS to the major tubercle of humerus HJ). It is believed that almost any combination of positions of the leg pairs $h_{L-R}$ and $f_{L-R}$ may be used to identify the skeletal trunk length L of the animal's body or the center of gravity defining the skeletal trunk size. In addition to determining skeletal trunk length L, the width of one or more single leg silhouettes (e.g., 92) corresponding to the metacarpus and metatarsus of the legs may be further used as a separate measurement to indicate bone diameter.

The disclosed system determines a scaled skeletal trunk length l of the animal from the recorded image 90. The disclosed system first calculates a relative distance $d_H$ between the hind leg pair $h_L$ and $h_R$, and calculates a relative distance $d_F$ between the fore leg pair $f_L$ and $f_R$ from the image 90. The image 90 may be or may be converted to a digital image, for example, composed of a plurality of pixels. The pixel size of the image 90 and the relative number of pixels per square inch or length may be known, for example. Thus, the disclosed system can determine distances by computer iterations that count separation between or widths of the silhouettes based on changes in contrast between individual pixel values to determine the relative distances $d_H$ and $d_F$. These and other techniques for processing images are known in the art. The relative distances $d_H$ and $d_F$ can then be divided to determine their midpoints $M_H$ and $M_F$. The separation between the midpoints $M_H$ and $M_F$ can then be calculated.

The separation between the midpoints $M_H$ and $M_F$ represents the scaled skeletal length l of the animal. To calculate an approximate skeletal length L of the animal using the scaled length l, the known angular view θ of the optical sensor 74, the scaled length l, and the known or average distance D of the optical sensor 74 from the animal A are used, where:

$$L \cong l + 2D \tan\left(\frac{\theta}{2}\right).$$

This formula is based on geometrical calculation. However, determining the skeletal length L of the animal using the scaled length l can be performed using a scale factor derived experimentally. For example, the width of the opposing light source 72 is known as well as the distance between the light source 72 and the optical sensor 74. Using these known values, the scale of the image 90 can be determined empirically.

With the location of the hind legs $h_L$ and $h_R$ identified, the disclose system activates the vertical and lateral ultrasound transducers 50 and 60, 62. When activated, the ultrasound transducers 50 and 60, 62 obtain distances from the individual devices 50 and 60, 62 to the body of the animal. In the present arrangement, the two lateral ultrasound transducers 60, 62 are simultaneously activated to obtain a measurement of the pelvic width $W_P$ of the animal. The vertical ultrasound transducer 50 is activated to obtain a measurement of the pelvic height $H_P$ of the animal. These measurements are sent to the software program in the processing system for interpretation.

The lateral ultrasound transducers 60, 62 each implement an ultrasonic wave, which is reflected when encountering the animal A. The ultrasound transducers 60, 62 receive the reflected signal. The speed of the sound waves is then divided by the travel times between the transmission and reception of the ultrasonic signals in order to approximate the respective distances $d_1$ and $d_2$ from the ultrasound transducers 60, 62 to the animal. Knowing the separation $d_3$ between the lateral ultrasound transducers 60, 62, the approximate pelvic width $W_P$ of the animal can be obtained, where:

$$W_P \cong d_{3(BetweenTransducers 60,62)} - (d_1 + d_2).$$

In a similar fashion, the approximate pelvic height $H_P$ of the animal is calculated using the known height H of the vertical ultrasound transducer 50 and the measured distance $d_4$ that the transducer 50 is from the pelvic region of the animal, where:

$$H_P = H_{(Transducer 50)} - d_4.$$

After the above calculations are performed, the disclosed system 80 in FIGS. 1–2B has the approximate weight $W_{kg}$, pelvic height $H_P$, pelvic width $W_P$, and skeletal trunk length L of the animal.

The values $H_P$, $W_P$, and L provide an approximate, 3-dimensional geometric measurement (width, height, length) of the skeletal size of the animal. The skeletal measurements $H_P$, $W_P$, and L are very reflective of an individual animal's body tissue carrying capacity and growth potential, which can be useful in managing the cattle and in estimating the animal's skeletal size and rate of growth. An animal's skeletal trunk length L is a better indicator of bone growth and is a better predictor of mature body weight than shoulder or hip height, because animal skeletal growth is greater longitudinally than vertically. Using known mathematical techniques or equations in the art, a skeletal coefficient for the animal can then be calculated using the skeletal dimensions of the animal. When the age of the animal is known, a frame score may be selected for future reference and assessment. As is known, skeletal size collected over time and/or frame score are parameters that can be used to describe an animal's growth potential. Typically, an animal's frame score changes very little as the animal matures. If age of the animal is approximated, measurements can be obtained throughout a feeding program to assign a frame score to the animal. A number of measurements may be required in younger animals to estimate their frame score. Because the determination of a frame score for an animal is dependent upon the height, age, and sex of the animal, a parameter of skeletal size or a coefficient of the skeletal growth rate of the animal may be used instead of frame score to differentiate the uniqueness of the animals.

The processing system 80 in FIGS. 1–2B can record and display data and results of calculations in a number of different manners. In one embodiment, for example, the processing system 80 can include a display or printer that provides a read out of the stored, measured, and calculated data. It is preferred that the processing system 80 include software for calculating various aspects of the animal, such as frame score, skeletal coefficient, hip height, hip width, skeletal trunk length L, percent body fat and/or protein, etc. In addition, it is preferred that the processing system 80 store relevant data relating to variables used in the calculations, such as age, sex, breed, etc.

When an initial measurement for a specific animal identified visually or electronically is obtained with unknown age, the body skeletal size can be recorded by the disclosed system 10 and can be used as an initial reference for changes in size and weight of the animal obtained in subsequent measurements with the disclosed system 10. The subsequent measurement are preferably used to more accurately determine the rates of skeletal and body tissue growth, which can be used to determine a more accurate frame score or eventual live animal mature size. The repeated measurements provide predictable projections of animal skeletal growth rate for live animals (% bone, muscle, and fat) and eventual carcass end-point or quality measurements (% bone, muscle, and fat).

A person skilled in the art will appreciate, however, that the body condition or empty body weight fat of cattle can vary between animals with the same skeletal structure. Scoring cattle based on body condition (i.e., the body condition scoring (BCS) system) is an effective management tool used in the art. Problems associated with body condition can surface in several ways, such as parasite and disease susceptibility, carcass quality grade, etc. Carcass quality grade or specification, which is correlated to the body condition of the animal, represents the economic value of an animal's carcass based on the percentage of bone, muscle, and fat. Management decisions involving the nutrition of the cattle are important to achieve the best animal body condition and carcass quality grade. Therefore, using body condition scoring (BCS) with the disclosed system 10 can aid in nutrition management of the cattle. In this way, the disclosed system can be used to assess live cattle tissue composition and project how many days on feed are required (dependent upon energy density of the rations) to bring the cattle to a specific live tissue composition for eventual marketing of the animal's carcass.

As is known in the art, body condition scores describe the degree of "fatness" of a cow in a numerical range of 1 to 9, with 1 being very thin, 9 being excessively fat, and 5 being average. To use the BCS system effectively, an operator must understand which areas of the cow anatomy deposit fat and must account for a number of factors, such as pregnancy status, gut fill, hair coat, age, etc. Live weight of the cattle is not the determining factor for body condition and fat reserves. Animals can have different live weights but similar body condition scores. Likewise, animals of similar live weight may differ in body condition. Using the North American Cow Body Condition Scoring (BCS) system, for example, a "thin" cow weighing about 383-kg may have a frame score of 4 and a pelvic height of 1.27-m. This "thin" cow may have a BCS of 3, corresponding to about 11.3% empty body weight fat or 12.6% carcass fat. In contrast, a "fat" cow weighing about 522-kg may have the same frame score of 4 and the same pelvic height of 1.27-m. This "fat" cow may have a BCS of 7, corresponding to about 26.4% empty body weight fat or 29.1% carcass fat. In other words, the difference of 139-kg or 15.1% empty body weight fat is dependent upon total empty body weight fat of the cow and is independent of skeletal structure.

With the understanding that the body condition or empty body weight fat of cattle can vary between animals with the same skeletal structure, it is preferred that the measurement of the skeletal structure obtained with the disclosed system be interpreted with additional information of the cattle. Accordingly, a person skilled in the art will appreciate that the values $H_P$, $W_P$, and L obtained with the disclosed system along with the weight, age, breed, sex, and other physical characteristics of the cattle can be interpreted using a number of techniques known in the art. For example, the NRC Beef 1996 Model, the Cornell Model, Body Condition Scoring, and a number of other techniques based on various measurements of the animal are known in the art and can be used by the disclosed system.

Using measurements obtained from the disclosed system along with additional information from techniques known in the art, the disclosed system can further enable feedlot managers to manage, sort, and monitor animals. In one example, the percentage of body fat of the animal can be calculated from the skeletal size of the animal and their known weight. Establishing percentage of empty body weight due to body fat on the animal can then help in accessing health risks to the animal caused by stressful environments. For example, the empty body weight related to body fat indicates the physiological condition of the animal and their risk to central nervous distress (hormonal changes e.g. diabetes & hypothalamus control).

Knowing the frame score, growth potential, and other determining characteristics of the animal obtained with the disclosed system combined with techniques known in the art enables animal managers to also advantageously make a number of predictive assessments and decisions about the animals. In one example, determining characteristics of the animal obtained with the disclosed system can be used for feeding and sorting the animals. For example, growth potential of the animal can be used to predict an animal's rate of growth, days on feed, or energy requirements throughout the finishing period. By determining the growth rate of an animal through predictive equations, an appropriate feeding program to achieve eventual live animal tissue composition or carcass end-point (% bone, muscle, and fat) can also be calculated.

In another example, knowing the determining characteristics of the animal can help animal managers to allocate feed resources and to classify and sort animals into specific groups. These results could increase the value of the animals, reduce the cost of production, or both. For example, the required amount of feed energy to produce a desired weight gain with a specific percentage of live animal empty body weight fat or carcass percentage fat may be projected through calculations using models known in the art. It is further believed that using skeletal measurements obtained with the disclosed system and method, for example, can improve feeding management of cattle with compensatory gain or with "shrink"—the decrease in body weight due to water loss.

In yet another example, the determining characteristics, such as the growth potential of the animal, obtained with the disclosed system 10 can be used to determine the best application of growth promotants, such as the types and quantities of growth promotants or feed additive re-partitioning agents desired. Implants of hormone growth promotant (HGP), which are combinations of estrogenic and androgenic compounds, are used in the beef industry to increase bone and protein deposition, which subsequently suppresses fat deposition. Cattle are commonly treated with an implant HGP to increase bone and muscle deposition. A combination of implant HGPs may be used on an individual animal throughout its life. By assessing the skeletal growth rate for an animal with the disclosed system and method, an animal manager can select a specific implant HGP or combination of implant HGPs to achieve a desired tissue composition of the animal. The feed additive re-partitioning agents, such as beta-agonist, have an anabolic and carcass re-partitioning effect concomitant to the influence of an HGP. The feed additive re-partitioning agents act primarily to increase body protein (mainly skeletal muscle) and to decrease fat content. Within a feeding program, time period for accurately selecting the use of these products is dependent upon animal's growth potential, empty body weight fat, and eventual desired animal slaughter chemical end point. In a further example, knowing the body sizes of animals can be used to accurately stock the animals in defined housing spaces of a feedlot, such as housing pens, boat pens, outside pens, and transport trailers. Furthermore, determining characteristics obtained with the disclosed system 10 may also be used to select animals suitable for breeding purposes. For example, repeated skeletal measurements of the animals over time can help to select heifers and bulls for breeding purposes.

It will be appreciated that aspects of the disclosed system and method of the present disclosure can be used on animals other than cattle, such as pigs and even humans. The disclosed system and method could be modified for the monitoring of the optimum growth of the following farm animals: replacement dairy heifers, bulls, sheep, goats, and horses. For example, the rate of growth of dairy heifers could be significant in mammary gland development and other desirable characteristics. Early skeletal features of bulls and racehorses, for example, could be significant in the prediction of mature structural conformation, which are very important features in the performance of these animals.

Not only can the disclosed system and method be used to determine physical dimensions of an animal, but also the disclosed system and method can be used to position animals based on measurements made. For example, the disclosed system and method can be used to center a beef or swine carcass for automated splitting of the carcass in a meatpacking house. In addition, by making a determination of the leg positions and the pelvic height and width, for example, the disclosed system and method can be used to select an area on an animal for applying medical products, such as anthelmintics and tick or fly control, or to select an area on the animal for placing an ultrasound transducer to determine subcutaneous rib fat.

The foregoing description of preferred and other embodiments is not intended to limit or restrict the scope or applicability of the inventive concepts that were conceived of by the Applicant. In exchange for disclosing the inventive concepts contained herein, the Applicant desires all patent rights afforded by the appended claims. Therefore, it is intended that the invention include all modifications and alterations to the full extent that they come within the scope of the following claims or the equivalents thereof.

What is claimed is:

1. A system for measuring at least one physical feature of an animal, comprising:
   a light source at least partially backlighting a first portion of the animal, wherein the first portion includes at least a portion of the lower leg of the animal;
   a first ultrasound transducer arranged substantially vertical to the animal to determine an approximate standing height of a second portion of the animal; and
   an optical device opposing the light source and obtaining an image that includes a silhouette of the first portion of the animal.

2. The system of claim 1, further comprising a housing unit having at least one sidewall with the light source or optical device mounted thereon.

3. The system of claim 2, further comprising at least one entry port formed at an end of the unit.

4. The system of claim 2, further comprising a device arranged adjacent the head of the animal for positioning the animal within the housing unit.

5. The system of claim 1, wherein the light source comprises a plurality of light emitting diodes arranged in an array.

6. The system of claim 5, wherein the plurality of light emitting diodes are monochromatic.

7. The system of claim 1, wherein the optical device is selected from the group consisting of a photographic camera, a charged-coupled-device, a photodiode array, a CMOS optical sensor, a digital camera, a single dimension video camera, and a 2-dimensional video camera.

8. The system of claim 7, wherein the optical device comprises a lens for limiting the field of view.

9. The system of claim 1, further comprising a processor coupled to the optical device for analyzing the image.

10. The system of claim 9, wherein the processor determines a measurement of the physical feature from the image.

11. The system of claim 10, wherein the measurement includes a width of a leg, a separation between a pair of legs, a skeletal trunk length of the animal, a pelvic height of the animal, a pelvic width of the animal, a center of the animal, or a volume of the animal.

12. The system of claim 9, wherein the processor comprises a computer having software and data storage.

13. The system of claim 9, wherein the processor selects an area on the animal to apply a medical product or to determine subcutaneous fat with an ultrasound transducer.

14. The system of claim 1, wherein the second portion of the animal includes the pelvic region of the animal.

15. The system of claim 1, further comprising a second ultrasound transducer arranged substantially lateral to the animal to determine an approximate width of a third portion of the animal.

16. The system of claim 15, wherein the third portion of the animal includes the pelvic region of the animal.

17. The system of claim 15, further comprising a third ultrasound transducer arranged substantially opposing the second ultrasound transducer.

18. A system for measuring an animal having legs, comprising:
    means for obtaining an image of a lower portion of at least one or more legs of the animal, wherein the means for obtaining the image comprises means for at least partially backlighting the lower portion of at least one leg of the animal;
    means for determining an approximate standing height of a portion of the animal; and
    means for determining at least one approximate physical dimension of the animal from the image.

19. The system of claim 18, wherein the means for obtaining the image comprises means for capturing one or more silhouettes of the lower portion of the one or more legs of the animal.

20. The system of claim 18, wherein the physical dimension includes a width of a leg, a separation between a pair of legs, a skeletal trunk length of the animal, a pelvic height of the animal, a pelvic width of the animal, a center of the animal, or a volume of the animal.

21. The system of claim 18, wherein the means for determining the at least one approximate physical dimension comprises means for determining an approximate distance between at least one pair of legs in the image.

22. The system of claim 18, wherein the means for determining the at least one approximate physical dimension comprises means for determining an approximate width of at least one leg of the animal in the image.

23. The system of claim 18, wherein the means for determining the at least one approximate physical dimension comprises means for determining an approximate skeletal trunk length of the animal from at least two pairs of legs in the image.

24. The system of claim 23, wherein the means for determining the approximate skeletal trunk length of the animal comprises:
    means for determining first and second midpoints respectively between first pair and second pairs of legs in the image; and
    means for determining an approximate distance between the first and second midpoints.

25. The system of claim 24, further comprising means for scaling the approximate distance between the first and second midpoints to approximate the skeletal trunk length of the animal.

26. The system of claim 18, wherein the means for determining the approximate height comprises means for measuring an approximate distance from an ultrasound transducer to the portion of the animal.

27. The system of claim 18, further comprising means for determining an approximate width of a second portion of the animal.

28. The system of claim 27, wherein the means for determining the approximate width comprises means for respectively measuring approximate distances from a pair of substantially opposing ultrasound transducers to the second portion of the animal.

29. The system of claim 18, further comprising means for selecting an area on the animal to apply a medical product or to determine subcutaneous fat with an ultrasound transducer.

* * * * *